US010653831B2

(12) United States Patent
Willoughby et al.

(10) Patent No.: US 10,653,831 B2
(45) Date of Patent: May 19, 2020

(54) MEDICAMENT DELIVERY DEVICE

(71) Applicant: CONSORT MEDICAL PLC, Hemel, Hempstead (GB)

(72) Inventors: Alastair Willoughby, Cambridge (GB); Brad Howarth, London (GB); Ian Anderson, Dullingham (GB); Rachel Koppelman, Cambridge (GB)

(73) Assignee: Consort Medical, PLC, Hemel, Hempstead (GB)

(*) Notice: Subject to any disclaimer, the term of this patent is extended or adjusted under 35 U.S.C. 154(b) by 401 days.

(21) Appl. No.: 15/032,554

(22) PCT Filed: Oct. 27, 2014

(86) PCT No.: PCT/GB2014/053193
§ 371 (c)(1),
(2) Date: Apr. 27, 2016

(87) PCT Pub. No.: WO2015/063462
PCT Pub. Date: May 7, 2015

(65) Prior Publication Data
US 2016/0279323 A1 Sep. 29, 2016

(30) Foreign Application Priority Data
Oct. 28, 2013 (GB) .................. 1319005.3

(51) Int. Cl.
A61M 5/145 (2006.01)
A61M 5/315 (2006.01)
(Continued)

(52) U.S. Cl.
CPC .... A61M 5/14526 (2013.01); A61M 5/31515 (2013.01); A61M 5/1454 (2013.01);
(Continued)

(58) Field of Classification Search
CPC .............. A61M 5/155; A61M 5/14526; A61M 5/1454; A61M 5/16877; A61M 5/31515;
(Continued)

(56) References Cited

U.S. PATENT DOCUMENTS 2,605,765 A 8/1952 Kollsman
2,766,754 A * 10/1956 Hill ................... A61M 5/31511
604/222

(Continued)

FOREIGN PATENT DOCUMENTS

EP 1008359 A1 6/2000
EP 1782852 A1 5/2007
(Continued)

OTHER PUBLICATIONS

Patent Cooperation Treaty, International Searching Authority, "Notification of Transmittal of the ISR and the Written Opinion of the International Search Authority, or the Declaration"; dated Aug. 3, 2015.

(Continued)

Primary Examiner — Nathan R Price
Assistant Examiner — Justin L Zamory
(74) Attorney, Agent, or Firm — Taft Stettinius & Hollister LLP; Ryan O. White

(57) ABSTRACT

A medicament delivery device including a first container having a delivery outlet at a front end thereof and a first stopper axially moveable in the first container, the first stopper defining and separating a first chamber and a second chamber in the first container, where the first chamber is axially forwards of the first stopper and the second chamber is axially rearwards of the first stopper. The medicament delivery device further includes a second container having a second stopper axially moveable in the second container, the second stopper defining and separating a third chamber and (Continued)

a fourth chamber in the second container, where the third chamber is axially forwards of the second stopper and the fourth chamber is axially rearwards of the second stopper, and where the third chamber has a vent outlet in fluid communication with a venting chamber.

18 Claims, 5 Drawing Sheets

(51) Int. Cl.
   *A61M 5/168* (2006.01)
   *A61M 5/20* (2006.01)
(52) U.S. Cl.
   CPC ............... *A61M 5/16877* (2013.01); *A61M 2005/14513* (2013.01); *A61M 2005/2086* (2013.01); *A61M 2205/3334* (2013.01); *A61M 2206/22* (2013.01)
(58) Field of Classification Search
   CPC ........... A61M 2005/3143; A61M 2005/14513; A61M 2005/2086; A61M 2206/22
   See application file for complete search history.

(56) References Cited

U.S. PATENT DOCUMENTS

| | | |
|---|---|---|
| 2,895,773 A | 7/1959 | McConnaughey |
| 3,605,745 A | 9/1971 | Hodosh |
| 4,561,856 A * | 12/1985 | Cochran ............... A61M 5/155 604/143 |
| 5,024,664 A * | 6/1991 | Mitchell ........... A61M 5/14526 604/143 |
| 5,807,337 A * | 9/1998 | Yamada ............ A61M 5/14526 604/131 |
| 6,280,416 B1 * | 8/2001 | Van Antwerp .... A61M 5/14276 128/DIG. 12 |
| 2005/0045438 A1 * | 3/2005 | Keller .................... F16F 9/0227 188/282.5 |
| 2007/0112326 A1 | 5/2007 | Bosshard et al. |
| 2008/0033359 A1 | 2/2008 | Kazemzadeh |
| 2008/0171999 A1 | 7/2008 | Baplue et al. |
| 2008/0294110 A1 * | 11/2008 | Klein ................. A61M 5/1454 604/151 |
| 2012/0022499 A1 * | 1/2012 | Anderson ......... A61M 5/14248 604/506 |

FOREIGN PATENT DOCUMENTS

| | | |
|---|---|---|
| WO | 91/06338 A1 | 5/1991 |
| WO | 92/01484 A | 2/1992 |
| WO | 2005/092409 A1 | 10/2005 |
| WO | 2011/133823 A1 | 10/2011 |

OTHER PUBLICATIONS

Search Report for Priority Application No. 1319005.3, dated Nov. 8, 2013.
PCT Written Opinion of the ISA, dated Aug. 3, 2015.

* cited by examiner

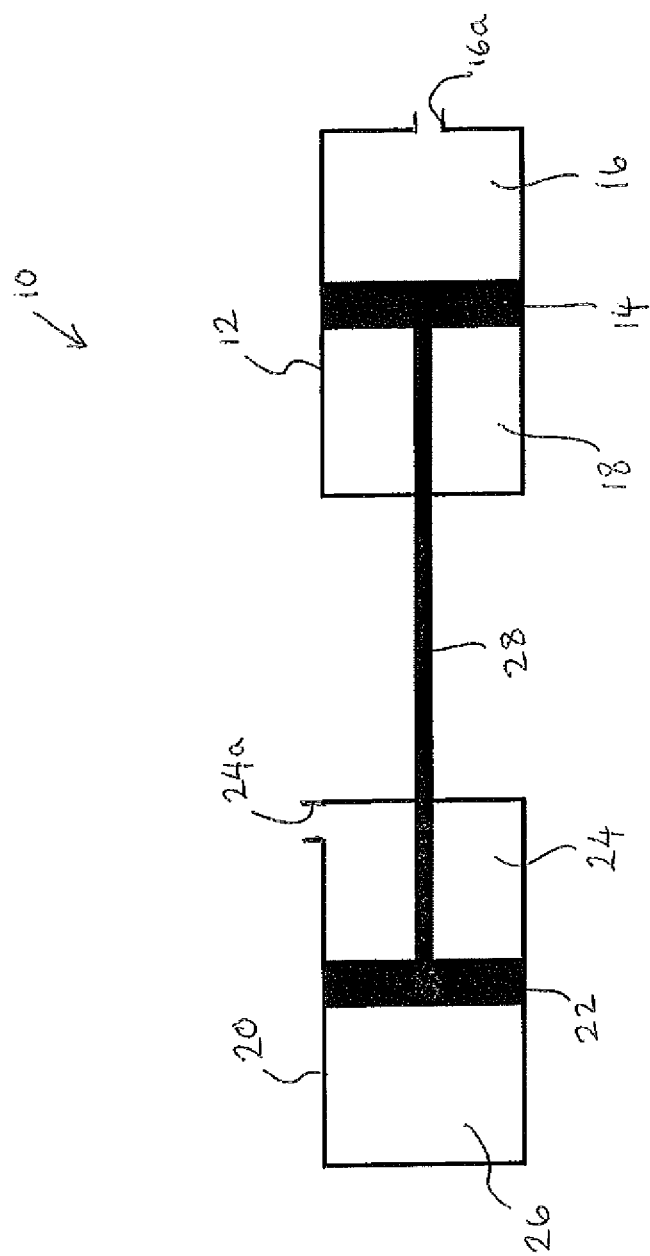

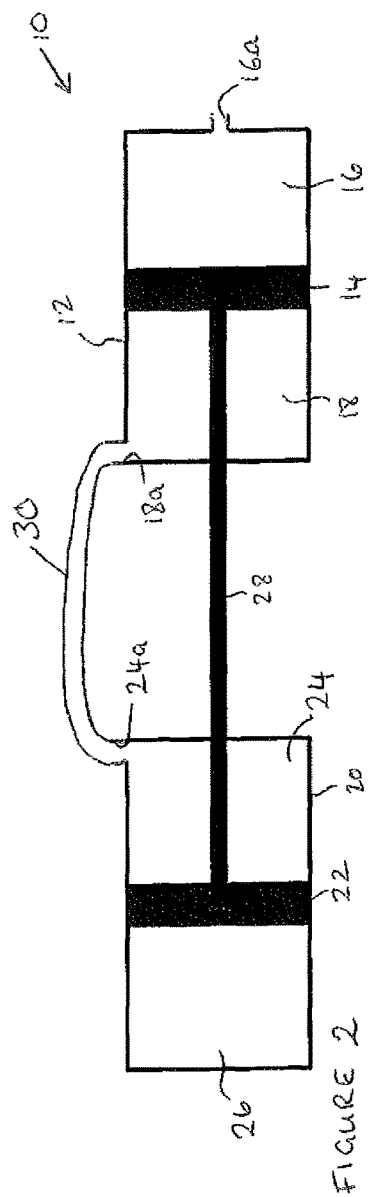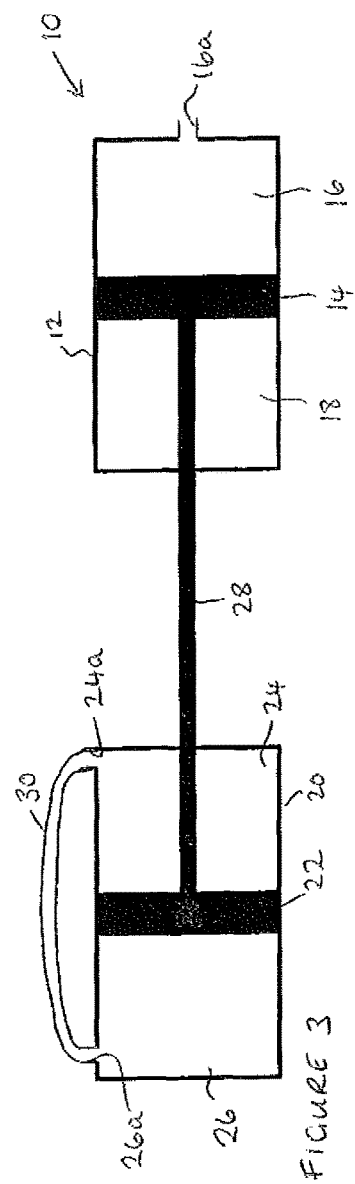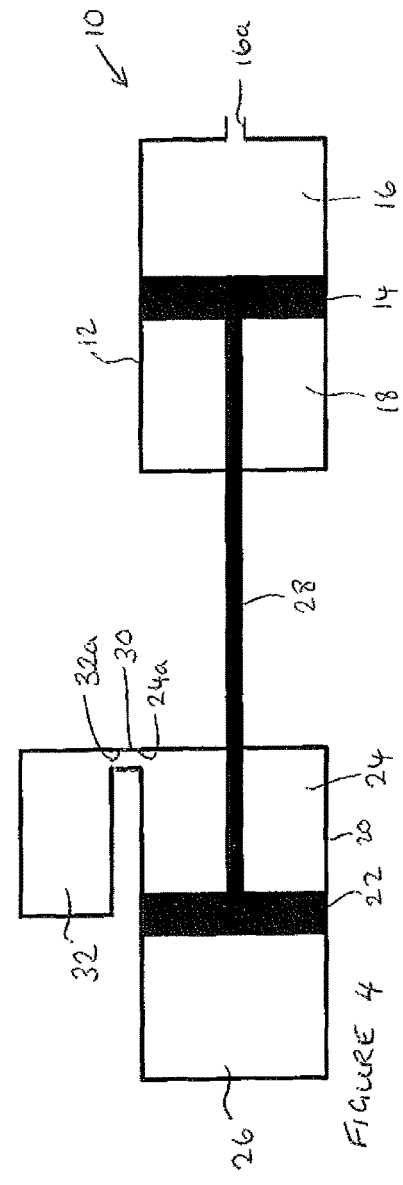

MEDICAMENT DELIVERY DEVICE

This application is a U.S. national stage application under 35 U.S.C. § 371 of PCT International Application Serial No. PCT/GB2014/053193 which has an international filing date of Oct. 27, 2014, designates the United States of America, and claims the benefit of GB Application No. 1319005.3, which was filed on Oct. 28, 2013. The disclosures of each of these prior applications are hereby expressly incorporated by reference in their entirety.

This invention relates to a medicament delivery device, and in particular, to a medicament delivery device for delivering medicament to a patient in a controlled manner.

BACKGROUND

Medicament delivery devices are generally known and include infusion-type devices which permit the slow delivery of medicaments to patients over long periods of time. One disadvantage of some prior art infusion devices is that they require an electrical power source or are large and cumbersome and inhibit the patient's mobility during a prolonged delivery. Indeed, it is preferable for a patient to be able to go about normal business during an infusion delivery, as far as possible.

An example of a known infusion device is described in US-A-2008/0033359 (Kazemzadeh). The described infusion device includes a control mechanism whereby motion of the plunger of the drug delivery syringe is controlled by a driver syringe having a piston or plunger for ejecting either a compressible or an incompressible fluid through a flow resistance element. A linkage is provided for coupling the piston of the drive syringe to the plunger of the drug delivery syringe.

It is an object of certain preferable embodiments of the present invention to provide a medicament delivery device that overcomes at least some of the disadvantages associated with the prior art. In particular, certain preferable embodiments of the present invention seek to provide a controllable and reliable medicament delivery device that further preferably may be a formed as a small, wearable device such that it minimizes disruption to the user during use.

BRIEF SUMMARY OF THE DISCLOSURE

In accordance with an aspect of the present invention there is provided a medicament delivery device comprising:

a first container having a delivery outlet at a front end thereof and a first stopper axially moveable in the first container, the first stopper defining and separating a first chamber and a second chamber in the first container, where the first chamber is axially forwards of the first stopper and the second chamber is axially rearwards of the first stopper; and a second container having a second stopper axially moveable in the second container, the second stopper defining and separating a third chamber and a fourth chamber in the second container, where the third chamber is axially forwards of the second stopper and the fourth chamber is axially rearwards of the second stopper, and where the third chamber has a vent outlet in fluid communication with a venting chamber;

wherein the first stopper is connected to the second stopper by a tensile member such that axially forwardly movement of the first stopper causes axially forwardly movement of the second stopper due to tensioning of the tensile member; and wherein the first stopper is driveable in an axially forwardly direction, the first chamber is configured to contain medicament for delivery through the delivery outlet as the first stopper moves axially forwards, the third chamber contains a viscous fluid that enters the venting chamber via the vent outlet as the second stopper moves axially forwards, and the fourth chamber has a pressure that is substantially equal to or greater than the pressure of the venting chamber;

such that as the first stopper is driven axially forwardly, the tensile member is tensioned and causes the second stopper to move axially forwardly and the venting of viscous fluid into the venting chamber via the vent outlet retards the axially forward movement of the second stopper and the first stopper.

Thus, the medicament delivery device of the present invention does not require an electrical power source, and yet is able to provide a controllable and reliable delivery of medicament over a period of time. Given that the tension in the tensile member is used to communicate the forward force acting on the first stopper to the second stopper, the tensile member may be made from a light and thin material. In particular, this may be possible since the tensile member is not required to perform any function under compression. Thus, the device may be made to be lightweight thereby further improving its suitability to be used as a wearable device that does not inhibit the wearer's movement or activity.

In one embodiment, each of the fourth chamber and the venting chamber may be configured to receive a propellant, wherein the propellant in the fourth chamber has substantially the same vapour pressure as the propellant in the venting chamber. In such an embodiment, the fourth chamber may be the venting chamber, or the venting chamber may be an independent chamber. More generally, the fourth chamber may be the venting chamber, and in certain embodiments, the vent outlet may pass through or around the second stopper to fluidly connect the third chamber to the fourth chamber. For example, the second stopper may include a needle passing therethrough such that a bore of the needle fluidly connected the third chamber to the fourth chamber. The vent outlet may be or include an aperture or a valved aperture or other restriction.

In an alternative embodiment, the vapour pressure in the venting chamber may be substantially equal to atmospheric pressure, and further, the venting chamber may be the external environment.

The device should be configured so that the pressure of the viscous fluid is greater than the pressure of the venting chamber to ensure that the viscous fluid is driven out of this chamber by the pressure gradient. Additionally, in some embodiments, the pressure of the viscous fluid is greater than the vapour pressure in the second chamber (e.g. where there is a shared boundary between the second and third chambers and a lower quality seal, or where the second chamber is the venting chamber).

In certain embodiments, the first container may be integrally formed with the second container.

In certain preferable embodiments, the tensile member may be a flexible tether. The flexible tether may pass over one or more deflection elements between said first stopper and said second stopper. The one or more deflection elements may include one or more rotatable pulleys. These arrangements may afford a particularly compact device since the first and second containers may be arranged side-by-side. This is particularly advantageous since it further improves the suitability of the device to be used as a compact, wearable device that minimizes disruption to the wearer.

The viscous fluid may have a viscosity of at least 0.1 Pa sec. In particular embodiments, the viscous fluid may have a viscosity of approximately 1 Pa sec, or between 0.1 and 1 Pa sec. In certain embodiments, the viscous fluid may be silicone oil or mixtures of glycerol and water.

In certain embodiments, the medicament delivery device may further comprise a needle in fluid communication with said delivery outlet.

In accordance with one embodiment, the second chamber may be configured to receive a propellant for providing a vapour pressure to the second chamber and driving the first stopper axially forwards. In particular, the medicament delivery device may further comprise a propellant source for providing said propellant (either to the second chamber or the fourth chamber, or both). The propellant may be a liquefied gas that boils to provide a vapour pressure. The propellant may be hydrofluoroalkane (HFA), and, in particular, may be HFA-134a or HFA-227. The use of a propellant is particularly advantageous since the absence of a mechanical or gas spring permits a device with a small footprint to be produced. This further enhances the device's suitability to be a wearable device that minimizes disruption to the wearer. Additionally, a propellant provides a constant force provided that there is enough thermal energy from its surroundings to permit vaporization (which is more likely to be the case for longer deliveries). Whilst the thermal energy available from the user/wearer's body (i.e. body temperature) is a potential source of heat for vaporizing the propellant, variations in body temperature and variations in the surrounding environment may give rise to pressure inconsistencies that may render the device inconsistent in use. One option for minimizing the effects of any temperature variability would be to use a propellant which boils significantly below the operating temperature. The controllability permitted by the present invention lends itself particularly well to the forces generated by propellant (particularly high pressure propellant), and this becomes more relevant for longer delivery periods. The high forces that may be generated by propellants are additionally advantageous in that frictional forces between the first stopper and first container (or second stopper and second container) are readily overcome and are substantially negligible in comparison. The use of propellants also allows the device to be stored in a non-stressed state (unlike a spring-powered device) and also permit a lighter device in comparison to a spring-powered device. A further advantage of utilizing propellant to drive the first stopper is that it increases the difficulty of re-using the device for multiple deliveries, in contrast to a spring device in which the spring may be recompressed. This minimizes the possibility of reuse or resetting of the device in cases where it is intended to be a single-use disposable device. Where the second chamber contains a propellant, the second chamber may also form the venting chamber.

In alternative embodiments, the first stopper may be drivable by a spring or by compressed gas.

The second stopper may comprise a deformable body having one or more radially flexible portions and a collar having a tapered portion proximate to the one or more radially flexible portions, wherein the collar is connected to the tensile member and axial movement of the collar relative to the deformable body causes the tapered portion to urge the one or more radially flexible portions against the tensile member and substantially seal the deformable body to the tensile member.

In accordance with another aspect of the present invention there is provided a stopper assembly for use in a medicament container, the stopper assembly comprising:

a stopper; and a tensile member for axially moving the stopper in the medicament container upon tensioning of the tensile member;

the stopper comprising a deformable body having one or more radially flexible portions and a collar having a tapered portion proximate to the one or more radially flexible portions;

wherein the collar is connected to the tensile member and axial movement of the collar relative to the deformable body causes the tapered portion to urge the one or more radially flexible portions against the tensile member and substantially seal the deformable body to the tensile member.

The stopper assembly may further comprise a fluidic channel in the deformable body for permitting a restricted flow of fluid from a first side of the deformable body to a second side of the deformable body. The fluidic channel may be formed by a bore of a needle disposed in the deformable body.

BRIEF DESCRIPTION OF THE DRAWINGS

Embodiments of the invention are further described hereinafter with reference to the accompanying drawings, in which:

FIG. 1 is a schematic representation of a medicament delivery device in accordance with an embodiment of the present invention;

FIG. 2 is a schematic representation of a medicament delivery device in accordance with an alternative embodiment of the present invention, in which the viscous fluid vents from the third chamber to the second chamber;

FIG. 3 is a schematic representation of a medicament delivery device in accordance with an alternative embodiment of the present invention, in which the viscous fluid vents from the third chamber to the fourth chamber;

FIG. 4 is a schematic representation of a medicament delivery device in accordance with an alternative embodiment of the present invention, in which the viscous fluid vents from the third chamber to an independent chamber;

DETAILED DESCRIPTION

Figure 5:
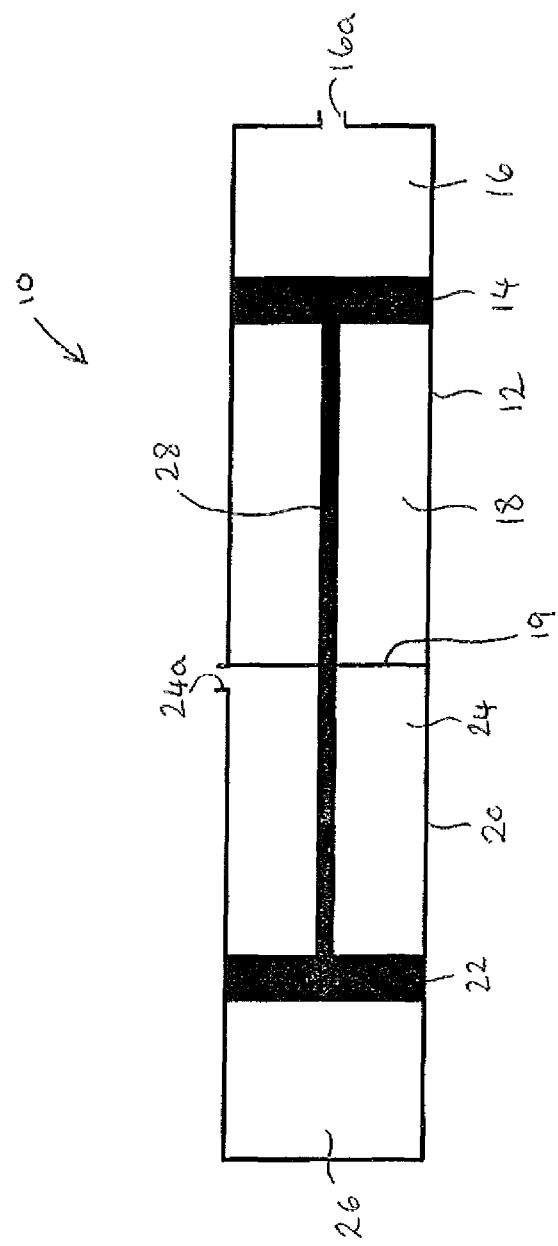
FIG. 5 is a schematic representation of a medicament delivery device in accordance with an alternative embodiment of the present invention, in which the first container is integral with the second container.

A medicament delivery device 10 in accordance with an embodiment of the present invention is shown schematically in FIG. 1. The medicament delivery device 10 includes a first container 12 and a second container 20. The first container 12 may be integrally formed with the second container 20 (as shown in FIG. 5, for example) or they may be separately formed components.

The first container 12 contains a first stopper 14 that is axially slidable therein. The first stopper 14 defines and sealingly separates a first chamber 16 and a second chamber 18 in the first container 12. In particular, the first chamber 16 is positioned axially forwards of the first stopper 14 and the second chamber 18 is positioned axially rearwards of the first stopper 14. At a forward end of the first container 12, there is a delivery outlet 16a in fluid communication with the first chamber 16. The delivery outlet 16a may be fluidly connected to a needle and this may be a direct connection or via a conduit, for example, a flexible hose. A flexible hose may permit the main body of the medicament delivery device 10 (i.e. the first container 12 and second container 20) to be held or worn at a more convenient or comfortable position away from the delivery site.

The second container 20 contains a second stopper 22 that is axially slidable therein. The second stopper 12 defines and sealingly separates a third chamber 24 and a fourth chamber 26 in the second container 20. The third chamber 24 is positioned axially forwards of the second stopper 22 and the fourth chamber 26 is positioned axially rearwards of the second stopper 22. The third chamber 24 has a vent outlet 24a in fluid communication therewith. In non-limiting preferable examples, the vent outlet 24a is disposed at or near a forward end of the third chamber 24, as shown in FIG. 1.

Figure 6:
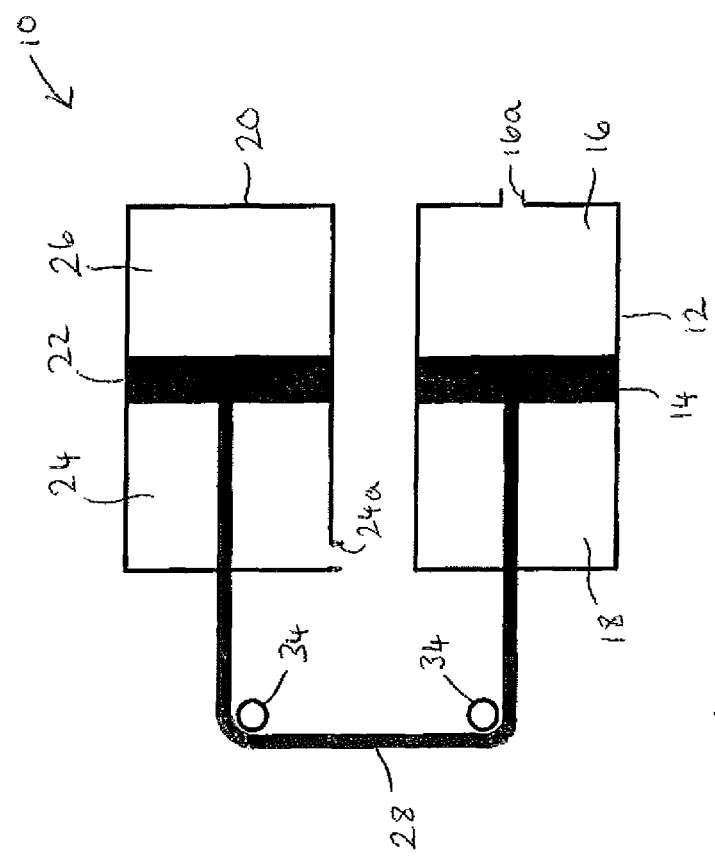
FIG. 6 is a schematic representation of a medicament delivery device in accordance with an alternative embodiment of the present invention, in which the first container is arranged side-by-side with the second container, with the connection member passing over deflection elements.

The first stopper 14 is connected to the second stopper 22 by a connection member 28. The connection member 28 acts such that axially forwardly movement of the first stopper 14 in the first container 12 causes axially forwardly movement of the second stopper 22 in the second container 20. The connection member 28 is a tensile member and in certain embodiments may be a tether which, further, may be flexible. In particular, it is not necessary for the connection member 28 to be a compressive member (i.e. such that axially forwardly movement of the second stopper 22 may cause axially forwardly movement of the first stopper 14). In the embodiment where the connection member 28 is a flexible tether, the tether may pass over one or more deflection members 34 so that the second container 20 may be arranged in a non-aligned position relative to the first container 12. For example, FIG. 6 shows a medicament delivery device 10 in accordance with an embodiment of the present invention in which the second container 20 is disposed by the side of the first container 12, with the connection member passing over a pair of deflection members 34. Such an arrangement affords a more compact assembly for the medicament delivery device 10. The one or more deflection members 34 may each be a static component (e.g. having a low friction surface), or a moveable component such as a rotatable pulley.

It should be noted that due to the potential non-linear arrangements of the device 10 of the present invention, the forward direction should be considered to be towards the direction of medicament delivery (i.e. the direction that the first stopper 14 must move in order to deliver medicament), and the rearward direction being opposite the forward direction. The longitudinal axis, to which 'axial' directions are relative, should be regarded as equivalent to the path of the connection member 28.

The connection member 28 passes through apertures in the surfaces of the first container 12 and second container 20. One or more seals are required to seal the surfaces of the first container 12 and second container 20 to the connection member 28 but permit movement of the connection member therethrough.

The second chamber 18 is configured to receive a propellant where the propellant provides a vapour pressure to the second chamber 18 that causes the first stopper 14 to move axially forwardly in the first container 12. In certain embodiments, the propellant may be or contain a hydrofluoroalkane (HFA) and, in particular, may be or contain HFA-134a. In preferable embodiments, liquid propellant may be provided to the second chamber 18 and subsequently boil (e.g. due to the thermal energy of its immediate surroundings) to produce a vapour pressure capable of causing the first stopper 14 to move axially forwardly in the first container 12.

The first chamber 16 is configured to receive a medicament for delivery to the patient. In particular, medicament contained in the first chamber 16 is pressurized upon axially forwardly movement of the first stopper 14 in the first container 12 causing the medicament to exit the first chamber 16 through the delivery outlet 16a.

The third chamber 24 contains a viscous fluid that is pressurized and forced from the third chamber 24 out of the vent outlet 24a upon axially forwardly movement of the second stopper 22 in the second container 20. The vent outlet 24a is fluidly connected to a notional venting chamber. As described in further detail below, the venting chamber may simply be the external environment (i.e. vent to atmosphere), it may be one of the second chamber 18 or fourth chamber 26, or it may be an independent self-contained chamber. In preferable embodiments the viscous fluid has a viscosity of at least 0.1 Pa sec. Examples of suitable viscous fluids include silicone oil, and mixtures of glycerol and water. The viscous fluid flowing out of the vent outlet 24a will be driven by the pressure drop across this outlet. The volumetric flow rate is determined in accordance with the Hagen-Poiseuille equation. Therefore, the flow rate (which determines the damping effect) may be manipulated by varying any of the viscosity of the viscous fluid, the magnitude of the pressure drop and the dimensions of the vent outlet 24a (and any further conduit connected thereto). As an example, a viscous fluid with a viscosity of 0.1 Pa sec could provide a medicament delivery of around 2 minutes if passing through a 0.5×13 mm (25 G×0.5") vent outlet 24a.

The fourth chamber 26 is required to have a vapour pressure that is substantially equal to or greater than the vapour pressure of the venting chamber. For example, if the vent outlet 24a vents to atmospheric pressure, then the vapour pressure in the fourth chamber 26 should be substantially equal to or greater than atmospheric pressure.

Additionally, it is preferable for the pressure of the viscous fluid to be greater than the pressure of the second chamber 18. This is particularly important in embodiments where the first container 12 and second container 20 are integrated and share a common wall between the second chamber 18 and third chamber 24 (a detailed discussion of an example of such an embodiment is provided below with reference to FIG. 5). One way of ensuring that the pressure of the viscous fluid is greater than the pressure of the second chamber 18 (or venting chamber) would be to pressurize the fourth chamber 26. In the absence of a pressurized fourth chamber 26, the pressure within the third chamber 24 will be lower than that of the second chamber 18, as shown in the equation:

$$P_3 = \frac{P_2 A - F_{friction}}{A},$$

where $P_3$ is the pressure in the third chamber 24, $P_2$ is the pressure in the second chamber 18, $F_{friction}$ is the friction experienced by the moving first and second stoppers 14, 22 and the friction due to passing through sealing members and A is the cross sectional areas of the first and second stoppers 14,22.

Adding additional pressure to the back of the second stopper 22 (i.e. to the fourth chamber 26) increases the pressure in the third chamber 24 to:

$$P_3 = \frac{P_2 A + P_4 A - F_{friction}}{A}.$$

By ensuring that the fourth chamber 26 is pressurized, in the case where the third chamber 24 is venting into a pressurised venting chamber (e.g. the second chamber 18 or a pressurised fourth chamber 26), there is an appropriate pressure gradient to force the viscous fluid through the vent outlet 24a.

In use, medicament is contained in the first chamber 16 and propellant is provided to the second chamber 18. As the propellant provides a sufficient vapour pressure to the second chamber 18, the first stopper 14 is caused to move axially forwardly in the first container 12 and pressurize the medicament in the first chamber 16, subsequently causing the medicament to exit through the delivery outlet 16a towards the delivery site.

As the first stopper 14 moves axially forwardly in the first container 12, the second stopper 22 is caused to move axially forwardly in the second container 20 due to the connection member 28. As the second stopper 22 moves axially forwardly in the second container 20, the viscous fluid in the third chamber 24 is pressurized and subsequently vents out of the third chamber 24 through the vent outlet 24a. Given that the vapour pressure in the fourth chamber 26 is substantially equal to or greater than the vapour pressure of the notional venting chamber into which the viscous fluid vents via the vent outlet 24a, the pressure drop across the vent outlet 24a is reduced which, in turn, reduces the flow rate of viscous fluid through the vent outlet 24a.

This limitation on the flow rate of the viscous fluid out of the third chamber 24 inhibits forwardly axial movement of the second stopper 22 in the second container 20. Given that the second stopper 22 is connected to the first stopper 14 by connection member 28, the retardation of the second stopper 22 results in a retardation of the first stopper 14 which in turn reduces the delivery rate of medicament through the delivery outlet 16a. Thus, the rate of delivery is controlled and delivery may take place over a desired time period. The actual delivery rate will be determined by several factors including the diameter of the first container 12 and second container 20, the viscosity of the medicament, the size of the delivery outlet 16a, the viscosity of the viscous fluid in the third chamber 24, the size of the vent outlet 24a, and the pressure difference across the vent outlet 24a. These parameters can be tuned to provide the desired delivery rate, and hence delivery time period for a given volume of medicament.

FIGS. 2 to 4 show schematic representations of several specific embodiments of the present invention. In the medicament delivery device 10 of FIG. 2, the vent outlet 24a is fluidly connected to a vent inlet 18a of the second chamber 18 via a conduit 30. In this embodiment, the notional venting chamber is the second chamber 18. The vapour pressure in the fourth chamber 26 must therefore be substantially equal to or greater than the vapour pressure in the second chamber 18. Given that the vapour pressure in the second chamber 18 arises due to the propellant, the fourth chamber 26 may also contain the same propellant (or another propellant that produces the same vapour pressure).

In the medicament delivery device 10 of FIG. 3, the vent outlet 24a is fluidly connected to a vent inlet 26a of the fourth chamber 26 via conduit 30. In this embodiment, the notional venting chamber is the fourth chamber 26. Clearly, since the venting chamber is the fourth chamber 26, the vapour pressure in the fourth chamber 26 meets the requirement that it is substantially equal to or greater than the vapour pressure in the venting chamber. Indeed, the vapour pressure in the fourth chamber 26 will be exactly equal to the vapour pressure in the venting chamber.

In a related but alternative embodiment, the vent outlet 24a may be an aperture or valved aperture through the second stopper 22 which fluidly connects, or selectively fluidly connects (in the case of a valved aperture) the third chamber 24 and the fourth chamber 26 which becomes the venting chamber.

In the medicament delivery device 10 of FIG. 4, the vent outlet is fluidly connected to a vent inlet 32a of an independent venting chamber 32 via conduit 30. The independent venting chamber 32 is a self-contained chamber that is not fluidly connected to either of the second chamber 18 or fourth chamber 26. The vapour pressure in the independent venting chamber 32 may be at any value provided that it is lower than the pressure of the viscous fluid. Otherwise, the viscous fluid would not be able to flow from the third chamber 24 to the independent venting chamber 32. In any event, the requirement remains that the vapour pressure in the fourth chamber 26 is substantially equal to or greater than the vapour pressure in the independent venting chamber 32. For example, the independent venting chamber 32 may contain a propellant that provides a vapour pressure. In this case, the fourth chamber 26 may also contain a propellant that provides a vapour pressure to the fourth chamber 26 that is substantially equal to or greater than the vapour pressure in the independent venting chamber 32. In particular examples, the independent venting chamber 32 and the fourth chamber 26 may contain the same propellant, or they may both be at atmospheric pressure.

FIG. 5 shows an alternative of a medicament delivery device 10 in accordance with an aspect of the present invention wherein the first container 10 is integrally formed with the second container 20. In particular, a common wall 19 acts as a rear wall of the first container 10 and a front wall of the second container 20. This arrangement is preferable since it permits a single seal to be formed between the first container 12 and second container 20 and the connection member 28. This is in contrast to the arrangement of FIG. 1, for example, where one seal would be required to seal the first container 12 to the connection member 28 and another seal to seal the second container 20 to the connection member 28. Furthermore, by allowing the third chamber 24 and second chamber 18 to share a common boundary (i.e. the common wall 19), the pressure difference across the single seal can be minimized; this reduces risk of propellant leaking through the seal from the second chamber 18. When there is a common wall 19 between the third chamber 24 and second chamber 18, it may be preferable for the pressure of the viscous fluid to be greater than the pressure in the second chamber 18 regardless of whether or not the second chamber 18 is the venting chamber. Otherwise, propellant may leak from the second chamber 18 to the third chamber 24 through the seal. In this undesired case, the second stopper 22 may move axially rearwardly and the device 10 may fail to deliver medicament. Worse still, rearward movement of the second stopper 22 may cause bodily fluids form the patient to be drawn from the patient into the device 10. Of course, if the seal between the third chamber 24 and the second chamber 18 is good enough such that leakage is prevented across the seal, it is less important to have the pressure of the viscous fluid at a higher magnitude than the pressure of the second chamber 18. On the other hand, if the second chamber 18 is the notional venting chamber, the vent outlet 24a may actually be a leak path through the seal between the third chamber 24 and the second chamber 18. In this embodiment, there is no requirement to form a dedicated outlet in the surface of the third chamber 24.

Where any of the second chamber 18, fourth chamber 26 and independent venting chamber 32 contain a propellant, the propellant may be or contain a hydrofluoroalkane (HFA) and, in particular, may be or contain HFA-134a.

The medicament delivery device of the present invention may be wearable by a patient in the event that the controlled delivery of medicament is to take place over a long time period. Given that the present invention provides a controllable and reliable medicament delivery device that may be formed as a convenient compact apparatus, the medicament delivery device of the present invention may be worn by a user and minimize any disruption and inhibition typically associated with wearable infusion devices.

The medicament delivery device of the present invention is not limited to slow delivery of medicament (i.e. normally associated with infusion devices). Rather, the present invention provides a controllable and reliable device that is versatile, and that may be used to deliver a wide range of medicaments in a variety of manners. For example, the medicament delivery device of the present invention may be connected to a needle, an intra-venous line, or another other kind of device-patient interface associated with medicament delivery.

In alternative embodiments, the medicament delivery device of the present invention may be powered by power sources other than a propellant. For example, the first stopper 14 may be driven by a spring or a compressed gas.

Figure 7:
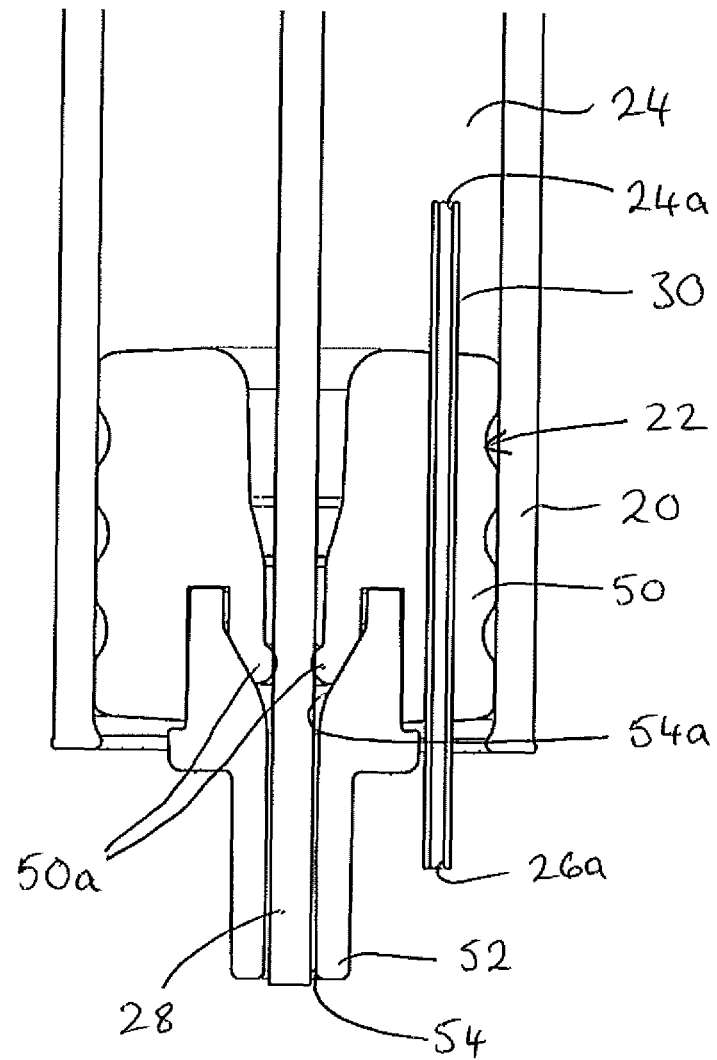
FIG. 7 shows a second stopper according to a particular embodiment of the present invention.

FIG. 7 shows a second stopper 22 in accordance with an embodiment of the present invention. The second stopper 22 comprises a deformable body 50 and collar 52. The deformable body 50 forms a seal against the wall of the second container 20 and has one or more radially flexible portions 50a that surround an aperture through which the connection member 28 passes. The collar 52 has a bore 54 therethrough for receiving the connection member 28, and the bore 54 widens radially along an axial direction to form a tapered opening 54a which surrounds the one or more radially flexible portions 50a. The connection member 28 is attached to the collar 52 such that tension in the connection member 28 leads to axial movement of the collar 52. The connection member 28 may be connected to the collar 52 by any suitable means, and may be connected, for example, by glue, welding or crimping.

Tensioning of the connection member 28 due to an applied force in the direction D indicated in FIG. 7 results in movement of the collar 52 against the initially stationary deformable body 50. The initial movement of the collar 52 relative to the deformable body 50 results in the radially inward urging of the one or more radially flexible portions 50a due to contact with the tapered opening 54a. Consequently, the inwardly urged one or more radially flexible portions 50a cause the connection member 28 to be substantially sealed against the deformable body 50 (and the deformable body 50 against the collar 52) such that fluid is substantially prevented from passing through the bore 54 of the collar 52. The skilled person will appreciate that the greater the force of the collar 52 against the one or more radially flexible portions 50a, the greater the compressive force of the one or more radially flexible portions 50a against the connection member 28. The above description with reference to FIG. 7 represents a particularly beneficial arrangement for connecting the connection member 28 to the second stopper 22, especially in embodiments wherein the connection member 28 to the second stopper 22 are made of dissimilar materials.

FIG. 7 also shows features of a further optional feature of the present invention which may be implemented independently or in addition to the specific embodiment of second stopper 22 described above in relation to FIG. 7. In particular, FIG. 7 additionally shows a needle serving as a conduit 30 to fluidly connect the vent outlet 24a with the vent inlet 26a of the fourth chamber through the second stopper 22. The needle forming the conduit 30 may be a tightly tolerance needle that is insert moulded into the second stopper 22.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A medicament delivery device comprising:
   a first container having a delivery outlet at a front end thereof and a first stopper axially moveable in the first container, the first stopper defining and separating a first chamber and a second chamber in the first container, where the first chamber is axially forwards of the first stopper and the second chamber is axially rearwards of the first stopper and configured to receive a propellant; and
   a second container having a second stopper axially moveable in the second container, the second stopper defining and separating a third chamber and a fourth chamber in the second container, where the third chamber is axially forwards of the second stopper and the fourth chamber is axially rearwards of the second stopper and configured to receive a propellant, and where the third chamber has a vent outlet in fluid communication with a venting chamber;

wherein the first stopper is directly connected to the second stopper by a tensile member such that axially forwardly movement of the first stopper causes axially forwardly movement of the second stopper due to tensioning of the tensile member; and wherein the first stopper is drivable in an axially forwardly direction, the first chamber is configured to contain medicament for delivery through the delivery outlet as the first stopper moves axially forwards, the third chamber contains a viscous fluid that enters the venting chamber via the vent outlet as the second stopper moves axially forwards, and the fourth chamber has a pressure that is substantially equal to or greater than the pressure of the venting chamber;

such that as the first stopper is driven axially forwardly, the tensile member is tensioned to pull the second stopper axially forwardly and the venting of viscous fluid into the venting chamber via the vent outlet retards the axially forward movement of the second stopper and the first stopper.

2. The medicament delivery device according to claim 1, wherein the venting chamber is configured to receive a propellant, and the propellant in the fourth chamber has substantially the same vapour pressure as the propellant in the venting chamber.

3. The medicament delivery device according to claim 1, wherein the fourth chamber is the venting chamber.

4. The medicament delivery device according to claim 3, wherein the vent outlet passes through or around the second stopper to fluidly connect the second chamber to the fourth chamber.

5. The medicament delivery device according to claim 1, wherein the pressure in the venting chamber is substantially equal to atmospheric pressure.

6. The medicament delivery device according to claim 5, wherein the venting chamber comprises the external environment.

7. The medicament delivery device according to claim 1, wherein the pressure of the viscous fluid is greater than the vapour pressure in the second chamber.

8. The medicament delivery device according to claim 1, wherein said tensile member is a flexible tether.

9. The medicament delivery device according to claim 8, wherein said flexible tether passes over one or more deflection elements between said first stopper and said second stopper.

10. The medicament delivery device according to claim 9, wherein said one or more deflection elements include one or more rotatable pulleys between said first stopper and said second stopper.

11. The medicament delivery device according to claim 1, wherein the viscous fluid has a viscosity of at least 0.1 Pa sec.

12. The medicament delivery device according to claim 1, wherein the second chamber is configured to receive a propellant for providing a vapour pressure to the second chamber and driving the first stopper axially forwards.

13. The medicament delivery device according to claim 2, further comprising a propellant source for providing said propellant.

14. The medicament delivery device according to claim 13, wherein said propellant is a liquefied gas that boils to provide a vapour pressure.

15. The medicament delivery device according to claim 13, wherein said propellant is hydrofluoroalkane (HFA).

16. The medicament delivery device according to claim 15, wherein said propellant is HFA-134a.

17. The medicament delivery device according to claim 12, wherein the second chamber is the venting chamber.

18. The medicament delivery device according to claim 1, wherein the second stopper comprises a deformable body having one or more radially flexible portions and a collar having a tapered portion proximate to the one or more radially flexible portions, wherein the collar is connected to the tensile member and axial movement of the collar relative to the deformable body causes the tapered portion to urge the one or more radially flexible portions against the tensile member and substantially seal the deformable body to the tensile member.

* * * * *